United States Patent [19]

Shave et al.

[11] Patent Number: 4,704,106
[45] Date of Patent: Nov. 3, 1987

[54] DRAINAGE DEVICE WITH DIVERTED GAS FLOW PATH

[75] Inventors: William H. Shave, Amityville; Joseph R. Williams, Floral Park, both of N.Y.

[73] Assignee: Pfizer Hospital Products Group, Inc., New York, N.Y.

[21] Appl. No.: 893,459

[22] Filed: Aug. 8, 1986

Related U.S. Application Data

[63] Continuation of Ser. No. 444,562, Nov. 26, 1982, abandoned.

[51] Int. Cl.$^4$ ............................................. A61M 1/00
[52] U.S. Cl. ..................................... 604/319; 604/321
[58] Field of Search .................. 137/205; 604/319–321

[56] References Cited

U.S. PATENT DOCUMENTS

| | | | |
|---|---|---|---|
| 4,015,603 | 4/1977 | Kurtz et al. | 128/276 |
| 4,261,362 | 4/1981 | Kurtz et al. | 128/276 |
| 4,296,748 | 10/1981 | Kurtz et al. | 128/276 |
| 4,312,351 | 1/1982 | Kurtz et al. | 128/276 |
| 4,324,244 | 4/1982 | Kurtz et al. | 128/276 |
| 4,396,386 | 8/1983 | Kurtz et al. | 604/318 |
| 4,425,125 | 1/1984 | Kurtz et al. | 604/321 |
| 4,453,937 | 6/1984 | Kurtz et al. | 604/319 |
| 4,468,226 | 8/1984 | Kurtz et al. | 604/321 |
| 4,533,353 | 8/1985 | Akiyama | 604/321 |

Primary Examiner—Stephen C. Pellegrino
Assistant Examiner—J. L. Kruter
Attorney, Agent, or Firm—Peter C. Richardson; Lawrence C. Akers; John L. LaPierre

[57] ABSTRACT

A drainage device has a collection chamber for receiving liquids and gases from the body of a patient, an underwater seal chamber and a one-way outflow valve. A partition extending across a portion of the device forms the underwater seal chamber, which prevents the flow of atmospheric air from the device into the pleural cavity of the patient, above the partition and the collection chamber below it. The underwater seal is created at the lower end of an extension connected to the inlet to the device by liquids drained from the patient. The one-way outflow valve communicates with a trap chamber for collecting liquids inadvertently conducted toward the valve. The trap chamber is closed off from the underwater seal chamber but is connected to the collection chamber by means of a passageway through a wall separating the trap and collection chambers.

5 Claims, 4 Drawing Figures

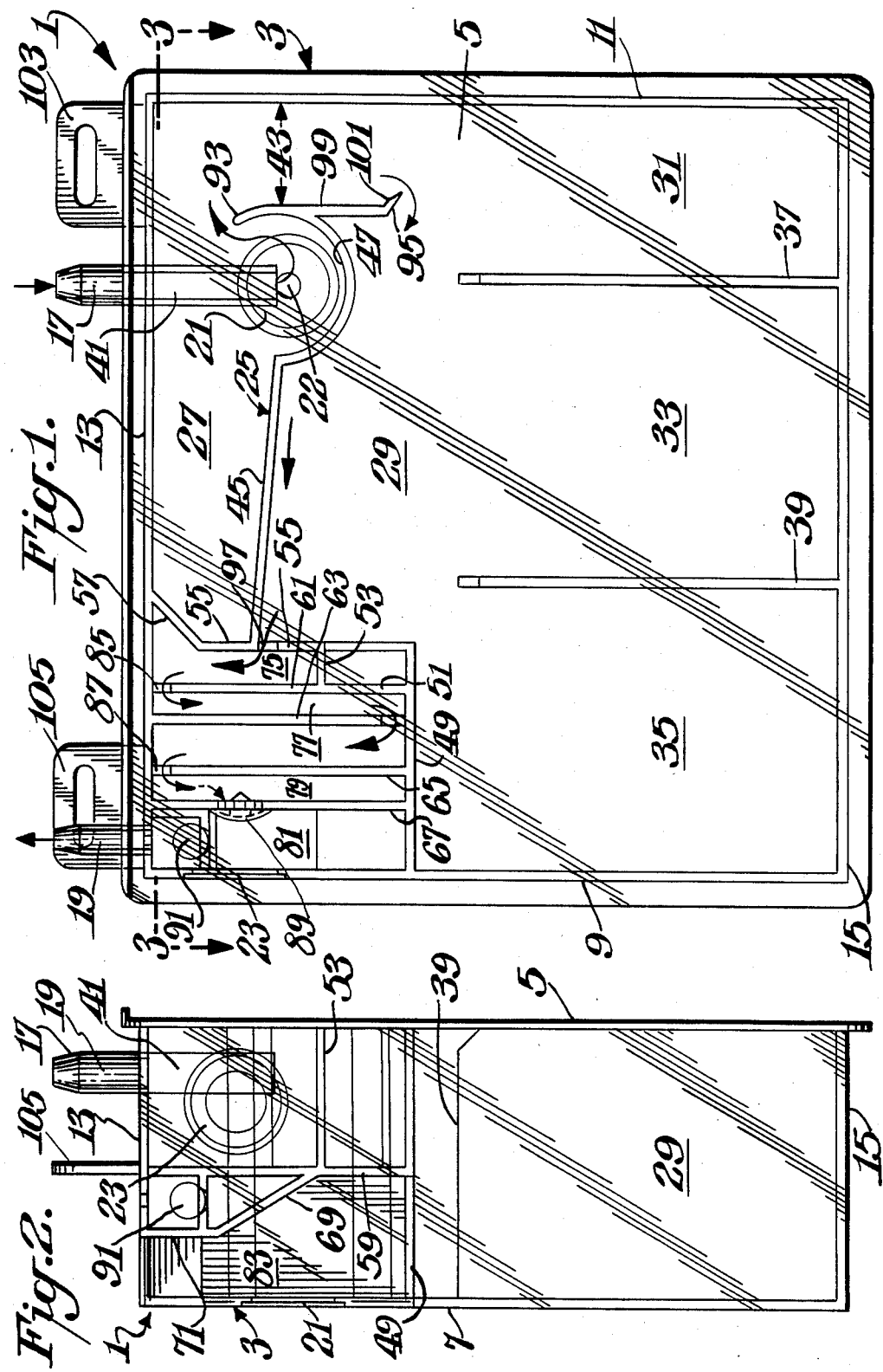

DRAINAGE DEVICE WITH DIVERTED GAS FLOW PATH

BACKGROUND OF THE INVENTION

This invention relates to a surgical drainage device which is designed to drain fluids from a body cavity such as the pleural cavity and to maintain proper pressures within the body cavity.

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as by lung surgery or by foreign objects which pierce the ribcage or, for example, where the patient has pleurisy, generates fluids in the pleural cavity which tend to obstruct normal breathing. It is necessary to provide a device which can remove these fluids from the pleural cavity and, at the same time, ensure that negative pressure is maintained within the pleural cavity.

Examples of one of the basic types of devices used for the above purposes are disclosed in U.S. Pat. Nos. 4,015,603; 4,261,362; 4,312,351 and 4,324,244. In this type of device an underwater seal chamber is formed at the top of the device by a wall or partition extending across a portion of the device. An underwater seal is created in the underwater seal chamber beneath the inlet to the device by liquids drained from the patient's body. The underwater seal serves as a diagnostic aid in the detection of leaks during inspiration in the pleural cavity or the drainage system. Also, it provides an additional barrier against the flow of atmospheric air from the device into the pleural cavity of the patient. Since the liquid seal does not have to be established by prefilling with water, this type of device is ideally-suited for use in emergency situations. Another important feature in this type of device is a one-way outflow valve located adjacent the outlet (which may be connected to a vacuum source or open to the atmosphere). This valve permits the escape of gases from within the device when the pressure therein is above that at the outlet but prevents the passage of atmospheric air into the device. As a result, the possibility of passage of atmospheric air or liquid from the liquid seal into the pleural cavity of the patient, of concern particularly during periods of high negative pressure in the pleural cavity, is greatly reduced.

However, a significant problem may sometimes arise with this type of device. Gases flowing from the pleural cavity of the patient through the liquid seal to the outlet may entrain relatively small amounts of the liquid in the seal and conduct it towards the one-way valve adjacent the outlet. This phenomenon tends to occur particularly when the liquid drained from the patient has a pronounced tendency to foam (e.g. blood and other proteinaceous liquids). Liquid contact with the one-way valve must be avoided since it can lead to impairment of the mechanical functioning of the valve.

SUMMARY OF THE INVENTION

The present invention comprises a novel drainage device comprising a housing, an inlet in the upper wall of said housing for liquids and gases from the body of a patient, a partition extending across a portion of the housing to form an underwater seal chamber above the partition and beneath the inlet and a collection chamber below the level of the partition for receiving said liquids and gases, with the partition being spaced from the housing to provide an opening to permit the flow of gases and liquids from the underwater seal chamber to the collection chamber, a tubular extension connected to the inlet and extending downwardly into the underwater seal chamber whereby liquids from the body of the patient are collected in the underwater seal chamber and provide a liquid seal with the lower end of the tubular extension, means for providing an outlet for gases from the housing, said outlet means including an outlet in the housing and a one-way valve for allowing the passage of gases in one direction only from the collecton chamber to the outlet, a trap chamber located between the inflow side of the one-way valve and the collection chamber for collecting liquids which are inadvertently conducted toward said valve, and a passageway connecting the collection chamber with the trap chamber. A critical feature of the present invention is that the underwater seal chamber is closed off from the trap chamber and the gas flow is diverted through the collection chamber. This diversion greatly reduces the possibility of conducting entrained liquid into the trap chamber and toward the one-way valve.

DETAILED DESCRIPTION OF THE INVENTION

The invention will be described in detail with reference to a preferred embodiment thereof. Reference to this embodiment does not limit the scope of the invention, which is limited only by the scope of the claims.

In the drawings:

FIG. 1 is a front elevation view of an underwater chest drainage device of the invention;

FIG. 2 is a left end elevation view of the drainage device of FIG. 1;

Figure 3:
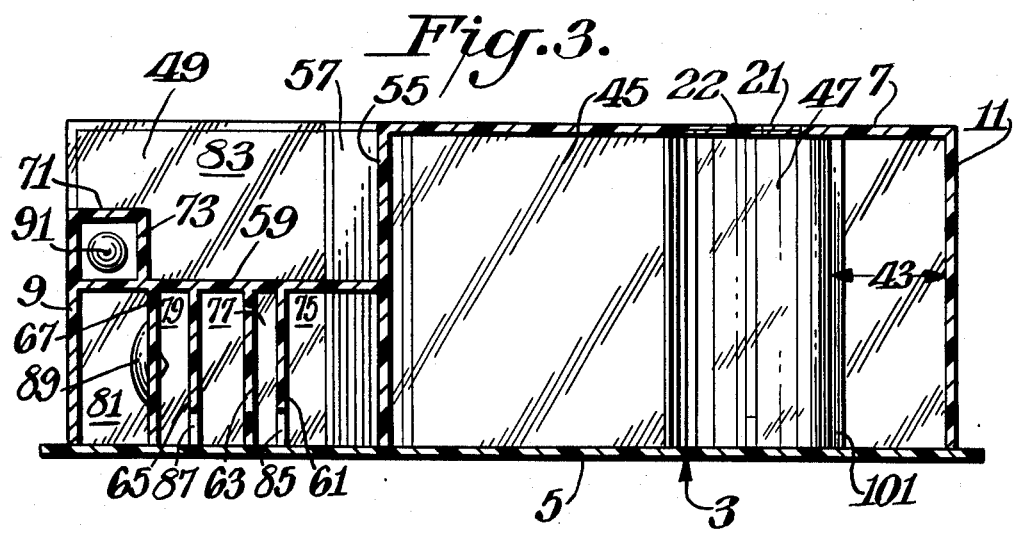
FIG. 3 is a section view taken along line 3—3 of FIG. 1.

A drainage device 1 of the present invention is shown in FIGS. 1 to 4. Device 1 comprises a generally box-shaped housing 3 having a front wall 5, a rear wall 7, end walls 9 and 11, a top wall 13 and a bottom wall 15. Housing 3, which is preferably made of a rigid transparent plastic material, is formed by bonding front wall 5 to a unitary piece comprising the other five walls of the housing. As shown in FIGS. 1 and 2, front wall 5 is provided with marginal portions extending beyond the points at which it is bonded to walls 9, 11, 13 and 15, for example by solvent welding.

Drainage device 1 is provided with an inlet 17 in top wall 13 for attachment to a thoracotomy tube which extends into the pleural cavity of the patient and an outlet 19 also in top wall 13 for attachment to a source of suction. (In certain modes of operation of the device, outlet 19 is left open to the atmosphere.) Housing 3 is also provided with two openings providing access to the interior of the housing. The first opening, which is in wall 9, provides access for the installation of one-way valve 89 during the manufacture of device 1. After said installation, this opening is closed by bonding cover 23 to wall 9. The second opening is closed by cover 21 in sealing engagement over a rubber grommet with wall 7. Cover 21 is provided with a central rubber portion 22.

This opening provides access, if desired, to prefill the underwater seal with water.

As is shown in FIG. 1, drainage device 1 includes an internal partition 25 extending across (from left-to-right in FIG. 1) a portion of housing 3. Partition 25, which extends the full distance between front wall 5 and rear wall 7, defines and forms an underwater seal chamber 27 between partition 25 and top wall 13 and beneath inlet 17. Additionally, partition 25 defines and forms beneath its level a collection chamber 29 for receiving liquids and gases from the patient's body. In the preferred embodiment of the invention shown in FIGS. 1 to 4, the main body of collection chamber 29 is divided into three collection wells 31, 33 and 35 by vertical walls 37 and 39.

Figure 4:
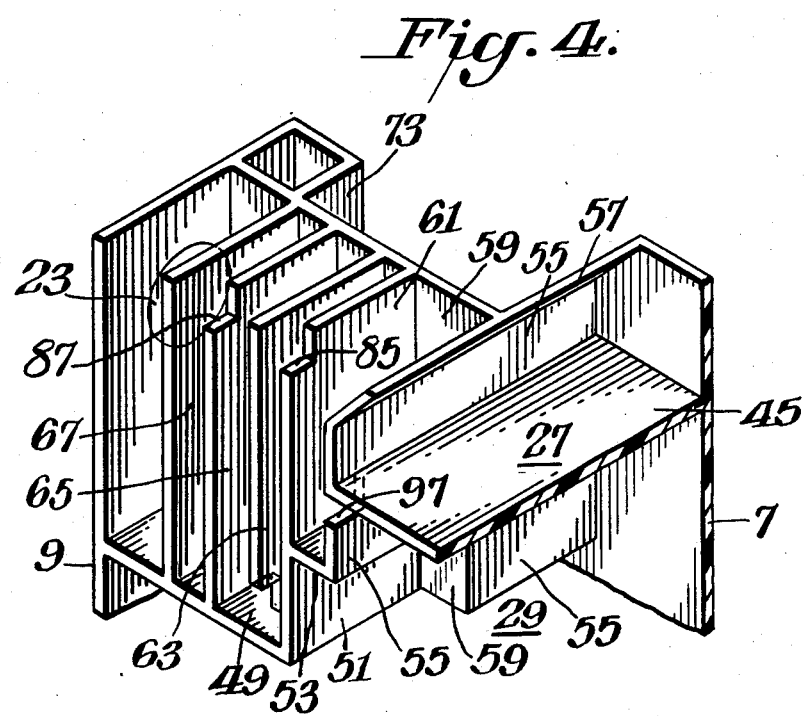
FIG. 4 is an enlarged perspective view of certain internal features of the drainage device of FIG. 1 adjacent the outlet of the device.

As is best shown in FIG. 1, drainage device 1 includes a tubular extension 41 connected to inlet 17 and extending downwardly therefrom into underwater seal chamber 27. As will be described in more detail below, liquids from the body of the patient are collected in underwater seal chamber 27 during the operation of device 1 and thereby provide a liquid seal with the lower end of tubular extension 41. As shown in FIGS. 1 and 4, partition 25 is spaced from end wall 11 to provide an opening 43 to permit the flow of gases and liquids from underwater seal chamber 27 to collection chamber 29. Preferably, as shown in the figures, partition 25 includes a substantially flat portion 45 gradually sloped (at about 2° to about 3°) downwardly towards a cup-like portion 47 located below the lower end of tubular extension 41. Cup portion 47 is sized so as to satisfy two somewhat conflicting criteria. The purpose of cup portion 47 is to retain liquid drained from the pleural cavity so that after a predetermined amount of liquid has been drained and the bottom of inlet tube 41 is covered, a seal is automatically formed. Thus, one criterion is that cup portion 47 be small enough so that only a relatively small amount of liquid needs to be drained from the pleural cavity of the patient before a seal is formed. On the other hand, it is an important feature of the present invention that the seal, once formed, not be destroyed by the inadvertent tilting of drainage device 1. Hence, cup portion 47 should have a sufficiently large capacity that should some liquid be lost therefrom, the seal will not be broken. The sloping of partition portion 45 permits the liquid accumulating in underwater seal chamber 27 to flow in the direction of cup portion 47. Device 1 is also provided adjacent opening 43 with a gate 93 extending above the end of cup-like portion 47 and a drip ledge 95 extending below the end of said portion.

Walls 49, 51, 53, 55 and 57 separate an upper corner of the interior of housing 3 from the remainder of said interior. Walls 55 and 57 also form the end of underwater seal chamber 27 opposite from opening 43. Additionally, internal walls 61, 63, 65 and 67, each of which extends between walls 5 and 59, further divide said inner corner into a trap chamber 75, a flow chamber 77, a connecting chamber 79 and an outflow chamber 81. These chambers are connected by passageway 85 (between chambers 75 and 77), passageway 87 (between chambers 77 and 79) and a one-way outflow valve 89 positioned on wall 67 (between chambers 79 and 81). As can be seen in FIGS. 1 and 4, wall 61 is a vertical extension of wall 51. Collection chamber 29 and trap chamber 75 are connected by means of passageway 97 in wall 55. However, no direct fluid connection is provided between underwater seal chamber 27 and trap chamber 75. The space generally defined beyond walls 49, 55, 57 and 59 which is designated in FIGS. 2 and 3 as 83 is exterior to device 1. A one-way outflow valve of suitable construction for use in the device of the present invention is disclosed in U.S. Pat. Nos. 4,312,351 and 4,324,244, which patents are incorporated herein by reference. When the pressure in underwater seal chamber 27, collection chamber 29, trap chamber 75, flow chamber 77 and connection chamber 79 exceeds the pressure in outflow chamber 81, one-way valve 89 is forced open so as to permit the passage of gases into outflow chamber 81 and to outlet 19. However, when the pressure is higher within outflow chamber 81 than within the remainder of drainage device 1, one-way valve 89 remains closed preventing gas flow in the opposite direction. Preferably, the device 1 includes a positive pressure relief valve 91, e.g. of the type described in the above-mentioned U.S. Pat. Nos. 4,312,351 and 4,324,244. The purpose of valve 91, which is shown in the figures of the present application as housed in fluid communication with outflow chamber 81 between walls 9, 13, 59, 69, 71 and 73, is to provide a means for the release of high positive pressure to the atmosphere in the event that very high pressures are inadvertently reached within the interior of the drainage device. The positive pressure relief valve remains closed during the normal operation of the drainage device. If desired, an air flow meter (not shown in the figures) for measuring the rate of flow of gases through the outlet may be located within flow chamber 77. This meter may be, for example, of the rising ball type.

If any liquid from underwater seal chamber 27 should inadvertently be carried by the gas flow through passageway 97, this liquid will collect in trap chamber 75 and thus be prevented from impairing the mechanical functioning of one-way valve 89 or, if present, an air flow meter in flow chamber 77. If sufficient liquid is collected in trap chamber 75, it will overflow through passageway 97 back into collection chamber 29.

When drainage device 1 is used, it is normally used with a suction from a regulated suction source attached to outlet 19. A hose from the regulated suction source is attached to outlet 19 and the desired degree of negativity is maintained within device 1 and the pleural cavity. However, in some situations device 1 can also be used without an external suction source. In either case, drainage device 1 may be used without prefilling the liquid seal. A thoracotomy tube (not shown in the figures) is connected between the pleural cavity of the patient and inlet 17. One-way outflow valve 89 prevents the passage of atmospheric air to the patient with the resulting danger of pneumothorax or contamination. The liquid secretions from the pleural cavity of the patient are initially collected in cup-like portion 47 of partition 25 and quickly form a liquid seal at the lower end of tubular extension 41. As additional liquid is collected, the liquid in the underwater seal chamber 27 overflows gate 93 and is then collected in collection chamber 29.

As drainage device 1 operates to collect fluids from the pleural cavity of the patient, liquids from the pleural cavity are collected in collection chamber 29 (in addition to the limited amount held in underwater seal chamber 27) while gases which are passed from the pleural cavity into drainage device 1 are subsequently conducted out of the device. These gases follow a flow path through inlet 17, tubular extension 41, underwater seal chamber 27, opening 43, collection chamber 29, passageway 97, trap chamber 75, flow chamber 77, connection chamber 79, one-way outflow valve 89, outflow chamber 81 and outlet 19 (note arrows in FIG. 1). Since underwater seal chamber 27 is closed off from trap chamber 75 by walls 55 and 57 and these two chambers are not in direct fluid communication with each other, flow of said gases from the underwater seal chamber 27 directly to the trap chamber 75 does not occur. Because of the prevention of direct gas flow between the underwater seal chamber and the trap chamber and the consequent diversion of the gas flow to the more indirect route through the collection chamber, the likelihood that any significant quantity of entrained liquid might be carried by the gas flow from the underwater seal chamber to the trap chamber is quite low, even when the liquid in the liquid seal has a pronounced foaming tendency. This likelihood is even further reduced because of the configuration of drip ledge 95, which comprises a substantially vertical portion 99 and a portion 101 extending under opening 43 at an oblique angle with respect to portion 99. Because of this drip ledge configuration liquid overflowing gate 93 is diverted in a direction toward wall 11, thereby insuring that collection wells 31, 33 and 35 will be filled with liquid in that order. This has two desirable consequences. First, during at least the early stages of a drainage procedure (until well 31 is filled) any liquid foam overflowing gate 93 will be diverted to and collected in well 31. This foam will be physically removed from the gas flow path (note arrows in FIG. 1) and will thus be given time to collapse before it can be swept toward passageway 97 as a gas-entrained liquid. Second, because of the sequential filling of wells 31, 33 and 35, the operating personnel can readily determine by brief observation the precise total quantity of liquid drained from the patient at any particular time during the operation of the device.

Another advantageous feature of the present invention is its stability against disruption of function by accidental tilting. Should housing 3 be inadvertently tilted towards wall 11, gate 93 serves to maintain liquid in underwater seal chamber 27. Since chamber 27 is closed off from trap chamber 75, liquids cannot escape from chamber 27 in the event of an inadvertent tilting of housing 3 towards wall 9. Thus, gate 93, wall 55, wall 57 and sloping portion 45 of partition 25 act together to maintain a sufficient reservoir of liquid in underwater seal chamber 27 to keep the liquid seal intact.

While drainage device 1 can rest on a table, floor, etc., it is preferred to provide one or more hanger attachments, such as attachments 103 and 105 to allow the device to be hooked onto a bedside or otherwise stabilized. Other suitable hanger arrangements that may be used to stabilize drainage devices of the present invention are disclosed in the above-mentioned U.S. Pat. Nos. 4,312,351 and 4,324,244.

A drainage device somewhat similar to drainage device 1 is known to the inventors herein and represents the point of departure for the present invention. The principal differences between the earlier device and drainage device 1 of the present invention are that the earlier device contains a gas flow passageway directly connecting the underwater seal chamber, rather than the collection chamber, with the trap chamber, and the drip ledge at the end of the partition in the earlier device does not include an obliquely-angled portion such as portion 101 in FIG. 1 herein. Although the earlier device is highly satisfactory in many applications, when the liquid in the liquid seal has a pronounced tendency to foam, excessive passage of liquid into the trap chamber is a far greater problem with the earlier device than with the improved device of the present invention.

We claim:

1. A drainage device comprising:

a housing having a horizontal top wall;

an inlet in the upper wall of said housing for liquids and gases from the body of a patient;

a substantially horizontally extending partition extending across a portion of said housing to form an underwater seal chamber above said partition and beneath said inlet and a collection chamber below the level of said partition for receiving said liquids and gases, with said partition being spaced from said housing to provide an opening to permit the flow of gases and liquids from said underwater seal chamber to said collection chamber;

a tubular extension connected to said inlet and extending downwardly into said underwater seal chamber whereby liquids from the body of the patient are collected in the underwater seal chamber and provide a liquid seal with the lower end of said tubular extension;

means for providing an outlet for gases from said housing, said outlet means including an outlet in said housing and a one-way valve for allowing the passage of gases in one direction only from the collection chamber to said outlet;

a trap chamber located between the inflow side of said one-way valve and said collection chamber for collecting liquids which are inadvertently conducted toward said valve, with said trap chamber and said underwater seal chamber being contiguous along a common internal vertical wall said vertical wall extending from a level below said underwater seal chamber to said horizontal top wall; and a passageway located below said underwater chamber in said vertical wall for gas flow connecting the collection chamber with said trap chamber, said passageway not including any portion of said device directly above said partition, with said passageway being an opening in said vertical internal wall in said device separating said collection chamber and said trap chamber, with a flow path of gases from the body of the patient being established, when the negative pressure at said outlet exceeds the negative pressure at said inlet, all of said gases being conveyed through said inlet, said tubular extension, below said underwater seal chamber, said opening, said collection chamber, said passageway, said trap chamber, said one-way valve and said outlet, in that order of sequence, and with said underwater seal chamber and said trap chamber not being in fluid communication with one another except along said flow path.

2. A drainage device of claim 1 wherein said outlet means comprise additionally a positive pressure relief valve located downstream of said one-way valve.

3. A drainage device of claim 1 comprising additionally an air flow meter located in said housing between said trap chamber and said one-way valve for measuring the rate of flow of gases through said outlet.

4. A drainage device of claim 1 wherein said substantially horizontal partition includes a substantially flat portion gradually sloped downwardly towards a cup-like portion located below the lower end of said tubular extension, with said opening being located between the end of said cup-like portion and said housing.

5. A drainage device of claim 4 wherein said collection chamber is divided by internal walls in said device into a plurality of collection wells adapted to be filled sequentially by liquids drained from the body of the patient, and said device comprises additionally, adjacent said opening, a gate extending above the end of said cup-like portion and a drip ledge extending below the end of said cup-like portion, with said drip ledge comprising a substantially vertical portion extending downwardly from said end and a portion extending under said opening at an oblique angle with respect to said substantially vertical portion.

* * * * *